United States Patent [19]

Kelner et al.

[11] Patent Number: 5,563,176
[45] Date of Patent: *Oct. 8, 1996

[54] ILLUDIN ANALOGS USEFUL AS ANTITUMOR AGENTS

[75] Inventors: Michael J. Kelner; Trevor C. McMorris, both of La Jolla, Calif.; Raymond Taetle, Tucson, Ariz.

[73] Assignee: The Regents of the University of California, Oakland, Calif.

[*] Notice: The term of this patent shall not extend beyond the expiration date of Pat. No. 5,439,936.

[21] Appl. No.: 276,169

[22] Filed: Jul. 15, 1994

Related U.S. Application Data

[63] Continuation-in-part of Ser. No. 15,179, Feb. 9, 1993, Pat. No. 5,439,936, which is a continuation-in-part of Ser. No. 606,511, Oct. 31, 1990, Pat. No. 5,439,942, which is a continuation-in-part of Ser. No. 416,395, Oct. 3, 1989, abandoned.

[51] Int. Cl.$^6$ .......................... A61K 31/12; C07C 49/403
[52] U.S. Cl. .......................... 514/691; 560/162; 560/255; 560/256; 568/374
[58] Field of Search .......................... 514/691; 568/374; 560/162, 255, 256

[56] References Cited

U.S. PATENT DOCUMENTS 5,436,936  8/1995  Kelner et al. .......................... 514/546

FOREIGN PATENT DOCUMENTS 62-23404  4/1986  Japan .......................... A61K 31/12

OTHER PUBLICATIONS

Anchel et al., "The Biogenesis of Illudin S and M In *Clitocybe Illudens,*" *Phytochemistry,* 9, 2339–2343 (1970).
Anchel et al., "Antibiotic Substances from Basidiomycetes. VII. Clitocybe Illudens," *Proc. Natl. Acad. Sci. USA,* 36 (5), 300–305 (1950).
Brandsteterova et al., "HPLC determination of a new anti-cancer agent (acylfulvene in serum," *Neoplasma,* 39 (6), 369–373 (1992).
Brandsteterova et al., "HPLC Analysis of Novel Anti-Cancer Agents–Illudins and Their Analogs," *J. Liquid Chromatography,* 16 (1), 115–125 (1993).
French et al., "Poisoning With the North American Jack O'Lantern Mushroom," *Clinical Toxicology,* 26 (1&2), 81–88 (1988).
Hanson et al., "Studies in Terpenoid Biosynthesis. Part XV. Biosynthesis of the Sesquiterpenoid Illudin M," *J.C.S. Perkin I,* 876–880 (1976).
Harttig et al., "Leaianafulvene, A Sesquiterpenoid Fulvene Derivative From Cultures of *Mycena Leaiana,*" *Phytochemistry,* 29 (12), 3942–3944 (1990).
Kelner et al., "Preclinical Evaluation of Illudins as Anticancer Agents," *Cancer Research,* 47, 3186–3189 (1987).
Kelner et al., "Preclinical Evaluation of Illudins as Anticancer Agents: Basis for Selective Cytotoxicity," *J. Natl. Cancer Inst.,* 82 (19), 1562–1565 (1990).
McMorris et al., "On the Mechanism of Toxicity of Illudins: The Role of Glutathione," *Chem. Res. Toxicol.,* 3 (6), 574–579 (1990).
McMorris et al., "Fungal Metabolites. The Structures of the Novel Sesquiterpenoids Illudin–S and M," *J. Amer. Chem. Soc.,* 87 (7), 1594–1600 (1965).
McMorris et al., "Structure–Activity Relationships of Illudins: Analogs with Improved Therapeutic Index," *J. Org. Chem.,* 57 (25), 6876–6883 (1992).
McMorris et al., "Structure and Reactivity of Illudins," *Tetrahedron,* 45 (17), 5433–5440 (1989).
Shimomura, Osamu, "The Role of Superoxide Dismutase in Regulating the Light Emission of Luminescent Fungi," *J. of Experimental Botany,* 43 (256), 1519–1525 (1992).
Tanaka et al., "Metabolism of illudin S, a toxic principle of *Lampteromyces japonicus,* by rat liver. I. Isolation and identification of cyclopropane ring–cleavage metabolites," *Xenobiotic,* 20 (7), 671–681 (1990).
Tanaka et al. "Metabolism by rat liver cytosol of illudin S, a toxic substance of *Lampteromyces japonicus.* II. Characterization of illudin S–metabolizing enzyme," *Xenobiotic,* 22 (1), 33–39 (1992).
Varki et al., "Cloned Low Metastatic Variants from Human Lung Carcinoma Metastases," *Anticancer Research,* 10, 637–644 (1990).
Walser et al., "Mode of Action of Illudin S," *Antimicrob. Ag. Chemother.,* 3 (3), 357–362 (1973).
Weinreb, "Fulvenes Derived from Illudin S," *Tetrahedron Ltrs.,* 38, 3489–3491 (1971).

*Primary Examiner*—Gary Geist
*Assistant Examiner*—Rosalynd A. Williams
*Attorney, Agent, or Firm*—Schwegman, Lundberg, Woessner & Kluth, P.A.

[57] ABSTRACT

Antineoplastic illudin analogs are provided of the formula:

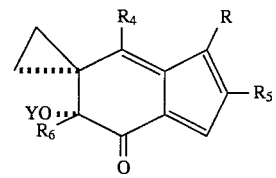

wherein $R_4$, $R_5$ and $R_6$ are $(C_1-C_4)$alkyl, Y is H, $(C_1-C_3)$alkyl, $(R_4)R_5)(R_6)$Si or alkanoyl $((C_1-C_4)$alkylC(O))$ and R is $CH_2OH$, halo, benzyl optionally substituted with OY, or alkanoylmethyl $(CH_2OC(O)R_7)$, wherein $R_7$ is $(C_1-C_4)$alkyl, $(C_6-C_2)$aryl or $N(X)_2$, wherein each X is H or $(C_1-C_4)$alkyl, and the pharmaceutically-acceptable salts thereof.

12 Claims, 6 Drawing Sheets

ILLUDIN ANALOGS USEFUL AS ANTITUMOR AGENTS

CROSS REFERENCE TO RELATED APPLICATIONS

This application is a continuation-in-part of U.S. Pat. No. 5,439,936, filed Feb. 9, 1993, which is a continuation in part of U.S. Pat. No. 5,439,942, filed Oct. 31, 1990; which is a continuation-in-part of abandoned U.S. patent application Ser. No. 07/416,395, filed Oct. 3, 1989, all of which are incorporated by reference herewith.

BACKGROUND OF THE INVENTION

This work was supported in part by research grant CA-37641 from the National Institute of Health. The U.S. Government has certain rights in the invention.

A listing of human cancers for which chemotherapy has exerted a predominant role in increasing life span, approaching normal life expectancy, includes Burkitt's lymphoma, acute lymphocytic leukemia and Hodgkin's disease, along with about 10–15 other tumor types. For example, see A. Golden et al., *Eur. J. Cancer* 17, 129 (1981) (Table 1). While the cure rate of these cancers illustrates the level of success of screening systems in selecting antitumor agents that are effective in man, these responsive tumors represent only a small fraction of the various types of cancer and, notably, there are relatively few drugs highly active against clinical solid tumors. Such drugs include cyclophosphamide, adriamycin, 5-FU, hexamethylmelamine and the like. Thus, patients with many types of malignancies remain at significant risk for relapse and mortality.

After relapse, some patients can be reinduced into remission with their initial treatment regimen. However, higher doses of the initial chemotherapeutic agent or the use of additional agents are frequently required, indicating the development of at least partial drug resistance. Recent evidence indicates drug resistance can develop simultaneously to several agents, including ones to which the patient was not exposed. The development of multiple-drug resistant (mdr) tumors may be a function of tumor mass and constitutes a major came of treatment failure. To overcome this drug resistance, high-dose chemotherapy with or without radiation and allogenic or autologous bone marrow transplantation can be employed. The high-dose chemotherapy may employ the original drug(s) or be altered to include additional agents. The development of new drugs non-cross resistant with mdr phenotypes is required to further the curative potential of current regimens and to facilitate curative interventions in previously treated patients.

Recently, the in vitro anti-tumor activity of a novel class of natural products called illudins was examined by Kelner, M. et at., *Cancer Res.*, 47, 3186 (1987), incorporated herein by reference. Illudin S and M are depicted below:

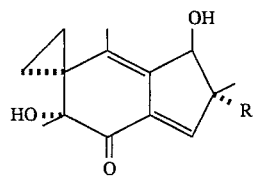

illudin S (R = CH$_2$OH)
illudin M (R = CH$_3$)

Illudin M was purified and submitted for evaluation to the National Cancer Institute Division of Cancer Treatment (NCI DCT) in vivo drug screening program. Illudin M significantly increased the life span of rats with Dunning leukemia, but had a low therapeutic index in solid tumor systems. The extreme toxicity of illudins has prevented any applications in human tumor therapy.

Thus, there exists a need for chemotherapeutic agents which are toxic to tumors, and especially to solid tumors, and which have an adequate therapeutic index to be effective for in vivo treatment.

SUMMARY OF THE INVENTION

The present invention provides cytotoxic illudin analogs of the general formula (I):

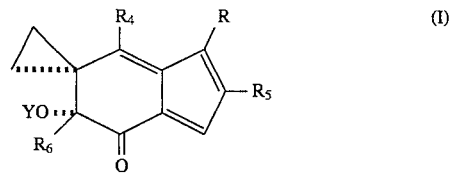

wherein $R_4$, $R_5$ and $R_6$ are $(C_1-C_4)$alkyl, Y is H, $(C_1-C_4)$alkyl, $(R_4)R_5)(R_6)$Si, or $(C_1-C_4)$alkylC(O) and R is $CH_2OH$, halo, benzyl optionally substituted with OY; $CH_2OCH_2OH$, or $CH_2OC(O)R_7$, wherein $R_7$ is $(C_1-C_4)$alkyl, $(C_6-C_{12})$aryl, or $N(X)_2$, wherein each X is H or $(C_1-C_4)$alkyl, and the pharmaceutically-acceptable salts thereof. These compounds are useful as antineoplastic agents, i.e., to inhibit tumor cell growth in vitro or in vivo, in mammalian hosts, and are particularly effective against multi-drug resistant tumors.

Preferably $R_4$, $R_5$ and $R_6$ are $CH_3$, Y is H or acetyl and R is

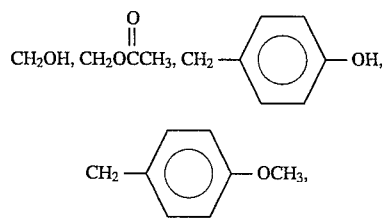

I or Br. For example, the compound of formula I wherein Y is H, $R_4$, $R_5$, and $R_6$ are $CH_3$ and R is $CH_2OH$ is referred to as 6-hydroxmethylacylfulvene, HMAF or as HMF. These compounds are unexpectedly active against solid tumors, as opposed to the rapidly growing tumor models such as P388, L1210 and B16. The present invention also provides a cytotoxic illudin analog of the formula H or III:

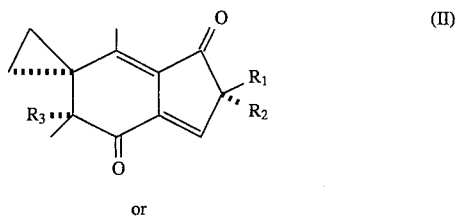

or

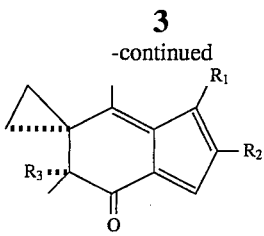

wherein the analog is capable of inhibiting tumor cell growth without excessive toxicity to the subject and wherein $R_1$ is $(C_1-C_4)$alkyl; $(C_1-C_4)$alkoxy or H, $R_2$ is $(C_1-C_6)$alkyl and $R_3$ is OY, wherein Y is as defined above. The compound of formula II wherein $R_1=R_2=CH_3$ and $R_3$ is OH is referred to as dehydroilludin M. Preferably, $R_1$ and $R_2$ are $CH_3$ and $R_3$ is OH. This analog is referred to as illudofulvene, and is depicted below (IV):

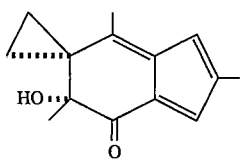

The illudofulvene dimer (V) is also an effective antitumor agent:

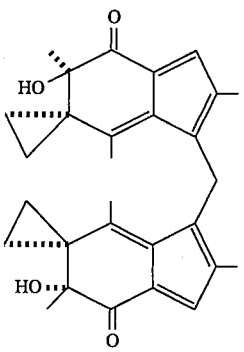

The present invention also provides cyotoxic compounds of general formula (VI):

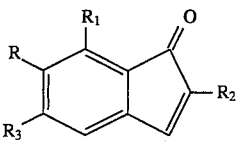

wherein R=methyl, and $R_1$, $R_2$ and $R_3$= $(C_1-C_6)$alkyl, preferably methyl, as well as cytotoxic compounds of the general formula (VII):

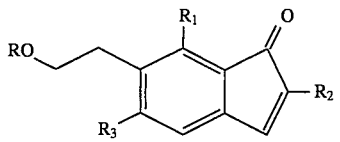

wherein R is H or methyl, and $R_1$, $R_2$ and $R_3$ are $(C_1-C_6)$alkyl, preferably methyl.

The present invention provides a therapeutic method to inhibit tumor cell growth in vitro, or preferably, in vivo, by administration to a mammal, such as a human cancer patient, of an amount of a compound of formula I–VII effective to inhibit the growth of said tumor cells. The present compounds may be particularly useful for the treatment of solid tumors for which relatively few treatments are available. Such tumors include epidermoid and myeloid tumors (myelomas) as well as lung, ovarian, breast and colon carcinoma. The present compounds can also be used against endometrial tumors, bladder cancer; lymphoma, Hodgkin's disease, B-cell leukemia, i.e., ALL, prostate cancer, sarcomas and testicular cancer as well as against tumors of the central nervous system, such as brain tumors and neuroblastomas. For example, HMAF is highly active in the MX-1 human xenograft breast cancer model currently employed to screen potential anticancer agents in the screening program at the Division of Cancer Treatment, National Cancer Institute. See, for example, A. Goldin et al., *Eur. J. Cancer,* 17, 129 (1981) for a description of the models used in this screening program. Thus, the present invention also provides pharmaceutical compositions, such as pharmaceutical unit dosage forms, comprising an effective anti-neoplastic amount of one or more of the present illudin analogs in combination with a pharmaceutically-acceptable carrier.

Applicants have made the surprising discovery that analogs of illudin S and M can be made which are less toxic than illudin S and M but are more effective chemotherapeutic agents in vivo. As noted above, illudin S and M have a low therapeutic index due to the extreme toxicity and, therefore, cannot be used therapeutically in humans. Applicants have discovered that various modifications in illudin S and M inhibit nucleophiles from reacting with the compound in vivo. This results in less facile opening of the cyclopropane ring which reduces the toxicity of the compound, resulting in a high therapeutic index.

As used herein, with respect to the present method, the term "inhibit" means either decreasing the tumor cell growth rate from the rate which would occur without treatment or causing the tumor cell mass to decrease in size. Inhibiting also includes causing a complete regression of the tumor. Thus, the present analogs can either be cytostatic or cytotoxic to the tumor cells.

The subject can be any mammal having a susceptible tumor, i.e., a malignant tumor. The analogs are effective on human tumors in vivo as well as on human tumor cell lines in vitro.

DETAILED DESCRIPTION OF THE INVENTION

Figure 1:
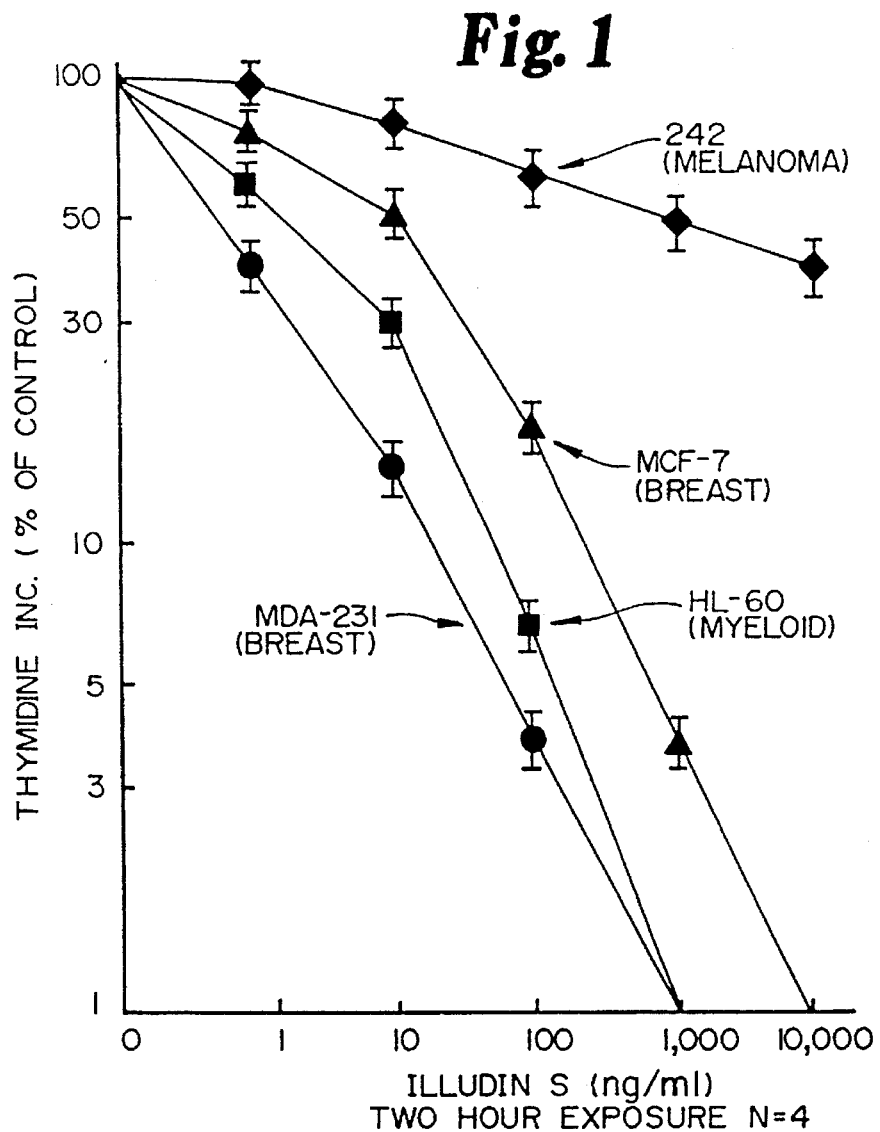
FIG. 1 shows the sensitivity of breast carcinoma and myeloid leukemia cells versus other tumors to illudin S.

As used herein, the term "alkyl" includes branched or straight-chain alkyl, including cycloalkyl and (cycloalkyl)alkyl, e.g., methyl, ethyl, isopropyl, n-butyl, isobutyl, cyclopropylmethyl, cyclopentylmethyl and the like.

As used herein, the term "aryl" includes mono- or bis-alkyl-substituted aryl, such as tolyl or xylyl; and ar($C_1$–$C_4$)alkyl, such as benzyl or phenethyl. Preferably, aryl is phenyl, tolyl or naphthyl.

Pharmaceutically-acceptable salts include, where applicable, salts such as amine acid addition salts and the mono-, di- and triphosphates of free hydroxyl groups. Amine salts include salts of inorganic and organic acids, including hydrochlorides, sulfates, phosphates, citrates, tartarates, malates, maleates, bicarbonates, and the like. Alkali metal amine or ammonium salts can be formed by reacting hydroxyaryl groups with metal hydroxides, amines or ammonium.

The preparation of the present compounds can proceed via fulvene (IV), and can be prepared from relatively simple starting materials, as depicted below:

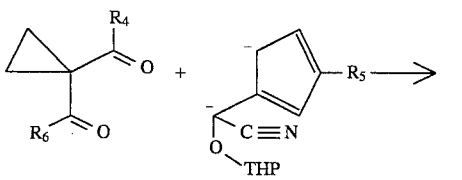

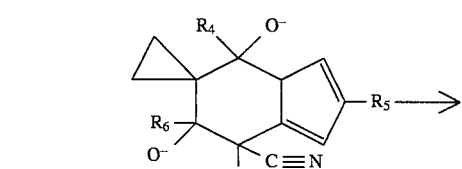

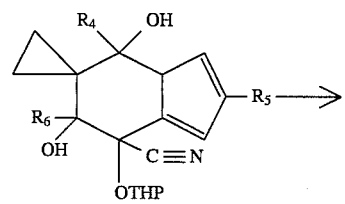

(THP = tetrahydroxopyranyl)

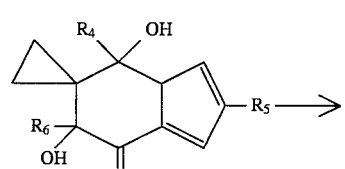

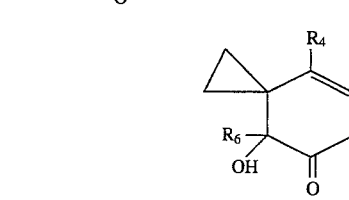

Reaction of the known 1,1-dialkanoyl cyclopropanes with the dianion of the cyclopentadiene derivative shown gives a diol which on mild acid treatment gives the diolketone. Selective elimination of a tertiary hydroxyl group gives the desired fulvene, wherein $R_4$, $R_5$, and $R_6$ are as described above.

Compounds of formula I can be prepared as outlined below:

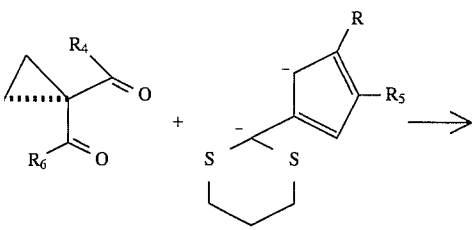

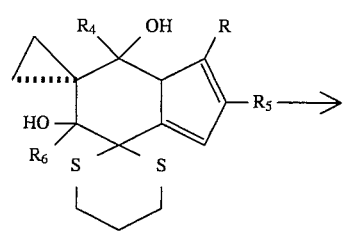

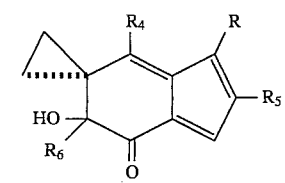

Aldol condensation of 1,1-diacetylcyclopropane with the dianion derived from an appropriately substituted cyclopentadiene gives an intermediate which is readily converted to the acylfulvene, wherein R, $R_4$, $R_5$, and $R_6$ are as described above.

The compounds of the present invention can be formulated as pharmaceutical compositions and administered to a mammalian host, such as a human cancer patient, in a variety of forms adapted to the chosen route of administration, i.e., orally or parenterally, by intravenous, intraperitoneal, intramuscular or subcutaneous routes.

Thus, the present compounds may be orally administered, for example, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of come, be varied and may conveniently be between 2 to about 60% of the weight of a given unit dosage form. The amount of active compound in such therapeutically useful compositions is such that an effective dosage level will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose, or saccharin or a flavoring agent such as peppermint, oil of wintergreen, or cherry flavoring may be added. When the unit dosage form is a capsule, it may contain, in addition to materials of the above type, a liquid carder, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmceutical dosage forms suitable for injection or infusion use can include sterile aqueous solutions or dispersions or sterile powders comprising the active ingredient which are adapted for the extemporaneous preparation of sterile injectable of infusible solution or dispersions. In all cases, the ultimate dosage form must be sterile, fluid and stable under the conditions of manufacture and storage. The liquid carrier or vehicle can be a solvent. For liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersion or by the use of surfactants. The prevention of the action of microorganisms can be brought about by various antibacterial and antifungal agents, or example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the corn positions of agents delaying absorption, for example, aluminum monostearate and gelatin. Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freezedrying techniques, which yield a powder of the active ingredient plus any additional desired ingredient present in the previously sterile-filtered solutions.

Useful dosages of the compounds of I can be determined by correlating their in vitro activity, and in vivo activity in animal models, such as murine or dog models, to activity in higher mammals, such as children and adult humans as taught, e.g., in Borch et al. (U.S. Pat. No. 4,938,949).

The therapeutically effective amount of analog necessarily varies with the subject and the tumor to be treated. However, it has been found that relatively high doses of the analogs can be administered due to the decreased toxicity compared to illudin S and M. A therapeutic amount between 30 to 112,000 µg per kg of body weight is especially effective for intravenous administration while 300 to 112,000 µg per kg of body weight is effective if administered intraperitoneally. As one skilled in the art would recognize, the amount can be varied depending on the method of administration.

The invention will be further described by reference to the following detailed examples.

EXAMPLE I

Synthesis of Dehydroilludin M.

A mixture of illudin M (200 mg) and pyridinium dichromate (1 g) in dry dichloromethane (60 ml) was stirred at room temperature in a flask equipped with a rubber septum so that an atmosphere of argon could be maintained. After 20 hours, the reaction mixture was diluted with diethyl ether (20 ml) and filtered through a short column of silica gel. The column was further eluted with more diethyl ether and the combined filtrate was concentrated, giving a residue which was chromatographed on silica gel with hexane-ethyl acetate (10:1) as eluent. The desired compound was obtained in early fractions from the chromatography. The yield was 140 mg of white crystals melting at 64°–65° C.

EXAMPLE II

Synthesis of Illudofulvene.

Illudin S 2g (9.2 mmol) was dissolved in 700 mL water followed by addition of 4 M $H_2SO_4$ (236 mL). The solution was stirred overnight, and extracted with ethyl acetate. The organic phase was washed with saturated $NaHCO_3$, water and brine, dried over $MgSO_4$ and concentrated. Chromatography on silica with hexane and ethyl acetate afforded 0.82 g illudofulvene (50%). $^1H$ NMR δ0.73 TO 1.50 (m, 4 H), 1.38 (s, 3 H), 2.00 (s, 3 H), 2.15 (s, 3 H),3.93 (s, 1 H), 6.43 (s, 1 H), 7.16 (s, 1 H); MS m/Z 216 (M+), 202 (M+-$CH_2$), 188 (M+-$CH_2CH_2$), 173 (M+-$2CH_2$-$CH_3$), 170 (M+-$2CH_2$-$H_2O$). UV 325 nm ($8.3 \times 10^3$), 235 nm ($16.6 \times 10^3$).

EXAMPLE III

In Vitro Studies

To assess cytotoxic effects, various concentrations of illudins were added to cultures of cells for 48 hours, then cell growth/viability was determined by trypan blue exclusion. As an alternative to 48 hour continuous exposure studies, cells were plated in liquid culture in 96 well plates, exposed to various concentrations of illudins for 2 hours, pulsed with [$^3H$]-thymidine for one to two hours and harvested onto glass filters. The filter papers were added to vials containing scintillation fluid and residual radioactivity determined in a beta (scintillation) counter.

When screening the sensitivity of other solid tumor cell lines to illudin S, a breast cell line, MCF-7, was noted to be markedly sensitive (FIG. 1). Another breast cell line maintained in our laboratory, MDA-231, was also found to be markedly sensitive to illudin S (FIG. 1).

Studies with dehydroilludin M indicated this analog also displayed selective toxicity towards myeloid leukemia cells and breast carcinoma lines MCF-7 and MDA-231 (Table 1).

TABLE 1

Histiospecific cytotoxicity of illudin S and dehydroilludin M as demonstrated by inhibition of thymidine after a two hour exposure to the toxins (N − 3).

| Cell Line | Illudin S | $IC_{50}$ (nM/L) Dehydroilludin M |
|---|---|---|
| HL60, myeloid | 7 ± 1 | 246 ± 19 |
| 8392, B-cell | 236 ± 31 | >38.000 |
| 8402, T-cell | 669 ± 196 | >38,000 |
| 242, melanoma | 607 ± 70 | >38,000 |
| 547, ovarian | 607 ± 110 | >38,000 |
| SL-2, murine (thymic) | 142 ± 15 | 5,235 ± 277 |
| MCF-7, breast | 58 ± 5 | 653 ± 65 |
| MDA-231, breast | 2.0 ± 0.2 | 112 ± 17 |

Became previous studies showed that CEM mdr variants were not resistant to illudin S, several other mdr cell types were studied for susceptibility to illudin S and the dehydroilludin M. These mdr daughter cell lines demonstrate a 200 to 800 fold increase in resistance to multiple conventional chemotherapeutic agents, but showed minimal or no resistance to illudin S or dehydroilludin M (Table 2). Thus, mdr cells associated with or without the gp170 protein were still susceptible to illudin toxicity. These studies indicate that illudins' novel structure confers relative non-cross resistance in multidrug resistant hematopoietic cell lines. The derivative of illudins, dehydroilludin M, is slightly less toxic than the parent illudin compound, but results (Table 2) indicate that there is no cross-resistance to this compound in various mdr cell lines.

The effect of illudin S and dehydroilludin M on L1210, murine bone marrow CFU-gm, and C1498 (AML cell line) was studied. Illudin S was the most potent agent ever tested in this assay and displayed the largest differential effect ever noted between L 1210 and AML leukemia lines and CFU-gm zone cites (Table 3). The derivative, dehydroilludin M, while less toxic-was markedly more selective towards the AML line. It inhibited AML colony formation at concentrations where it had no effect on the CFU-gm cells (Table 4).

TABLE 2

Sensitivity of Different Mdr lines to Illudin S

| MDR cell line available | | Illudin S | Dehydroilludin M |
|---|---|---|---|
| CEM | Parent | 8.3 ± 2.6 | nt* |
| Variants | VM-1 | 16.2 ± 6.4 | nt |
| | AraC | 14 | nt |
| | VLB100 (gp170+) | 3.7 ± 0.7 | nt |
| | Dox (gp170+) | 14 | |
| MDA-231 (Breast) | Parent | 0.85 ± 0.23 | 54 ± 7 |
| | 3-1 (gp170+) | 0.89 ± 0.38 | 58 ± 11 |
| MCF7-wt (Breast) | Parent | 0.88 ± 0.11 | 92 ± 15 |
| | ADR (GSH-transferase) | 3.7 ± 0.4 | 68 ± 15 |
| HL-60 | Parent | 3.1 ± 1.1 | 163 ± 11 |
| | ADR (gp150+) | 1.9 ± 0.8 | 191 ± 44 |
| KB variant | Parent | 0.58 ± 0.12 | 125 ± 14 |
| | C-1 (gp170+) | 0.69 ± 0.15 | 80 ± 18 |
| | VBL (gp170+) | 0.69 ± 0.11 | 78 ± 19 |
| L1210 | Parent | 0.42 ± 0.08 | 62 ± 8 |
| | DDPt (cis-plat) | 0.46 ± 0.12 | 119 ± 39 |
| | BCNU | 0.58 ± 0.08 | 100 ± 31 |
| | PAM (melphalan) | 0.62 ± 0.15 | 73 ± 31 |
| | CPA (cyclophos) | 0.46 ± 0.12 | 38 ± 15 |

*nt = not tested

TABLE 3

Inhibition of Growth by Illudin S

| Illudin S Concentration | Zone of Inhibition | | |
|---|---|---|---|
| (ug/disc) | L1210 | Go | Colon 38 |
| 2.50 | 500 | 240 | 30 |
| 1.25 | 400 | 70 | 0 |
| 0.63 | 320 | 3 | 0 |

TABLE 4

Effect of Illudins on Colony Formation

| Compound | Dilution | L1210 | Zone Size CFU-GM | C1498 (AML) |
|---|---|---|---|---|
| Illudin S | 1/1,000 | 850 | 400 | >1000 |
| | 1/4,000 | 600 | 200 | 800 |
| | 1/16,000 | 550 | 0 | 550 |
| | 1/64,000 | 300 | 0 | 250 |
| Dehydroilludin M | 1/25 | 400 | 200 | >100 |
| | 1/125 | 200 | 100 | 750 |
| | 1/125 (repeat) | 300 | 50 | 700 |
| | 1/625 | 100 | 0 | 400 |

EXAMPLE IV

Structure Function Studies.

Figure 2:
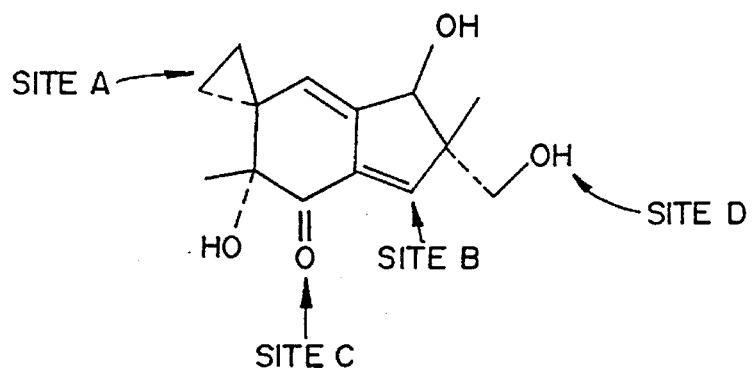
FIG. 2 shows the active sites of illudin S.

The structure-function studies were performed by synthesizing derivatives of the illudins and examining their in vitro toxicity for HL60 leukemia cells (Table 5). Ibis study identified three critical sites for illudin toxicity. These include the cyclopropane ring (site A), the alpha/beta unsaturated bond site (site B), and the ketone group (site C) (FIG. 2). Alteration of any of these sites resulted in up to a 4 log decrease in toxicity. In contrast, the non-ting primary hydroxyl group (FIG. 2, site D) does not contribute to toxicity. Various large chemical groups can be attached to this site without altering toxicity. Many of the derivatives with a marked decrease in toxicity (as compared to illudin S or M) are still more potent than conventional chemotherapeutic agents such as BCNU or cis-platinum (Table 5).

TABLE 5

$IC_{50}$ for Various Illudin Derivatives Versus Other Agents in HL-60 Cells

| COMPOUNDS | nM |
|---|---|
| Illudin S or M | 10 |
| Dehydroilludin S or M | 100,000 |
| Illudofulvene | 500 |
| Dehydroilludin M (diketone) | 246 |
| Isoilludin M | 3,800 |
| Ptaquiloside | 7,700 |
| Pterosin C | 12,500 |
| 2, 5, 6, 7-tetramethylindenone | 475 |
| Illudin tosylate | 38 |
| DNA polymerase inhibitor: Aphidocolin | 2,100 |
| Alkylating agent: BCNU | 23,300 |
| Crosslinking agent: cis-platinum | 550 ± 14 |
| Alkylating agent: MNNG | 15,000 |
| Protein Synthesis Inhibitor: Ricin | 0.2 |

EXAMPLE V

Structure-Function Studies: Chemical.

Figure 3:
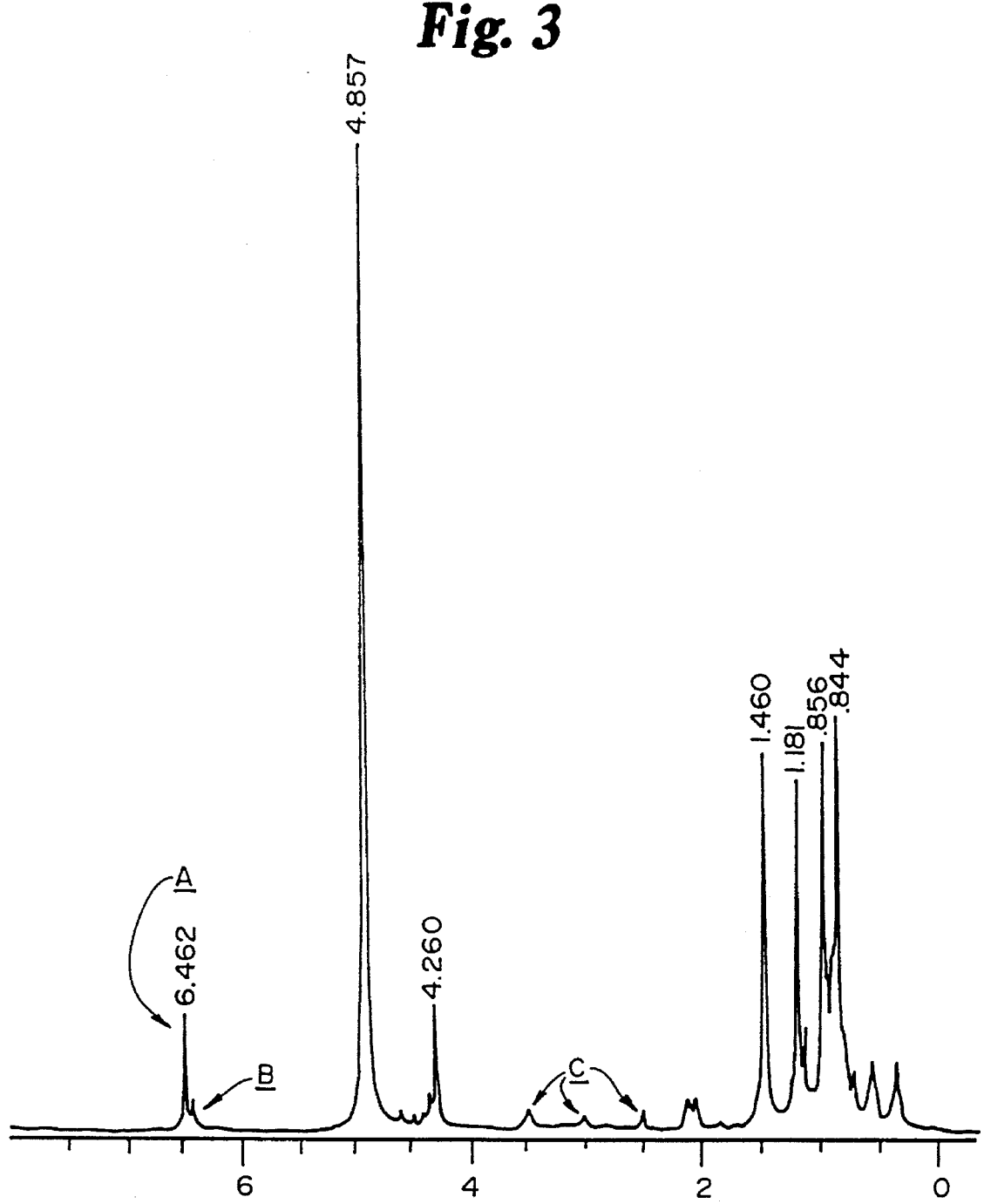
FIG. 3 shows an NMR spectrum demonstrating the presence of a short lived intermediate in acid. Signal A is from the hydrogen on the double bond in the 5 membered ring (illudin M). Signal B is from the hydrogen atom on the short lived intermediate that results from cyclopropane ring opening (but before the double bond reacts). Signals marked at C are from the product that results when the double bond has reacted. With time, the signal peaks from illudin M will disappear and the peaks at position C will be the predominant signals. Signal B will disappear concurrently with Signal A confirming it is a short lived intermediate arising from illudin M.

Illudin M is readily converted to stable aromatic compounds (on treatment with dilute HCl) which in cell culture studies are more than 1,000 fold less toxic. The chlorine-carbon bond formation, cyclopropane ting opening and extrusion of the tertiary hydroxyl (as water) are synchronous. The intermediate formed can be detected by NMR spectroscopy of the reaction mixture (FIG. 3). The intermediate, however, is highly reactive and is quickly converted to a phenol by attack of a second nucleophile, i.e., water. Thus, under acidic conditions, illudin M is clearly bifunctional.

The above studies indicate that the toxicity of illudins is related to the ease with which the tertiary hydroxyl can be removed and the cyclopropane ting opened. It was found that illudin toxicity depends on the combined effects of the cyclopropane group (site A, FIG. 2), the two double bonds (conjugated diene) (site B), and the ketone (site C). It was hypothesized that oxidation of the secondary hydroxyl group in the five membered ring to a ketone would alter the potency or selectivity of the molecule by contributing to rather electron delocalization within the molecule. The new ketone group acts as an "electron sink" so that electrons of the cyclopropane C-C bonds are delocalized towards the ketone rather than to the carbon atom bearing the tertiary hydroxyl. This means the incipient carbocation, forming as the carbon-oxygen (oxygen of the tertiary hydroxyl) bond breaks, is not as stable as in the case of illudin M. Therefore, carbon-oxygen bond breaking is less favorable and reactivity is reduced. This ketone derivative, termed dehydroilludin M, was synthesized and was less toxic to HL-60 cells in vitro than illudin S or M (Table 4). As discussed above, the toxicity of dehydroilludin M appeared relatively selective for myeloid and breast carcinoma cells in vitro (FIG. 1 and Table 1).

Consistent with the above hypothesis are the results of the kinetics of the reaction of illudin M and dehydroilludin M with dilute HCl. In dilute HCl, illudin M undergoes a pseudo first-order reaction ($k=4.7\times10^{-3}$, $t\frac{1}{2}$ =148minutes). Dehydroilludin M also demonstrated first-order kinetics but the reaction was considerably slower ($k=2\times10^{-4}$ min$^1$, t1/2= 2765 min). In the reaction with dehydroilludin M, no intermediate could be detected by NMR spectroscopy. Presumably it formed too slowly and is too short-lived to be detected. The lower reactivity shown by dehydroilludin M suggests it is more selective in its reaction with nucleophiles and thus has a lower toxicity compared to illudin M.

The reaction of illudins with a naturally occurring nucleophile, glutathione has also been studied.. At a wide pH range, from pH 3 to pH 9, glutathione spontaneously reacts with illudin M, illudin S, or dehydroilludin M, producing products analogous to those from the reaction of illudin M and HCl. The reaction rate is optimized at a pH of 6.1 to 7.0, indicating the reaction could occur intracellularly.

The toxicity of illudins toward a breast cell carcinoma line MCF7-wt and its MDR resistant daughter line MCF/Adr was then studied. The gp 170 negative daughter cell line is drug resistant in sensitivity to conventional chemotherapeutic agents. Ibis line also shows a 4.1 fold decrease in glutathione content. This daughter line showed a 4.2 fold decrease in sensitivity to illudin S (parent IC$_{50}$ 0.88 nmoles/l; daughter line 3.70 nanomoles/l) versus the 200 to 800 fold seen with other agents. Kinetic studies on the ability of illudins to inhibit glutathione transferase indicated there was no direct inhibition of enzyme activity. These findings show that while illudin toxicity is inversely correlated with intercellular glutathione content it is not correlated with glutathione transferase activity.

EXAMPLE VI

Animal Studies.

Figure 4:
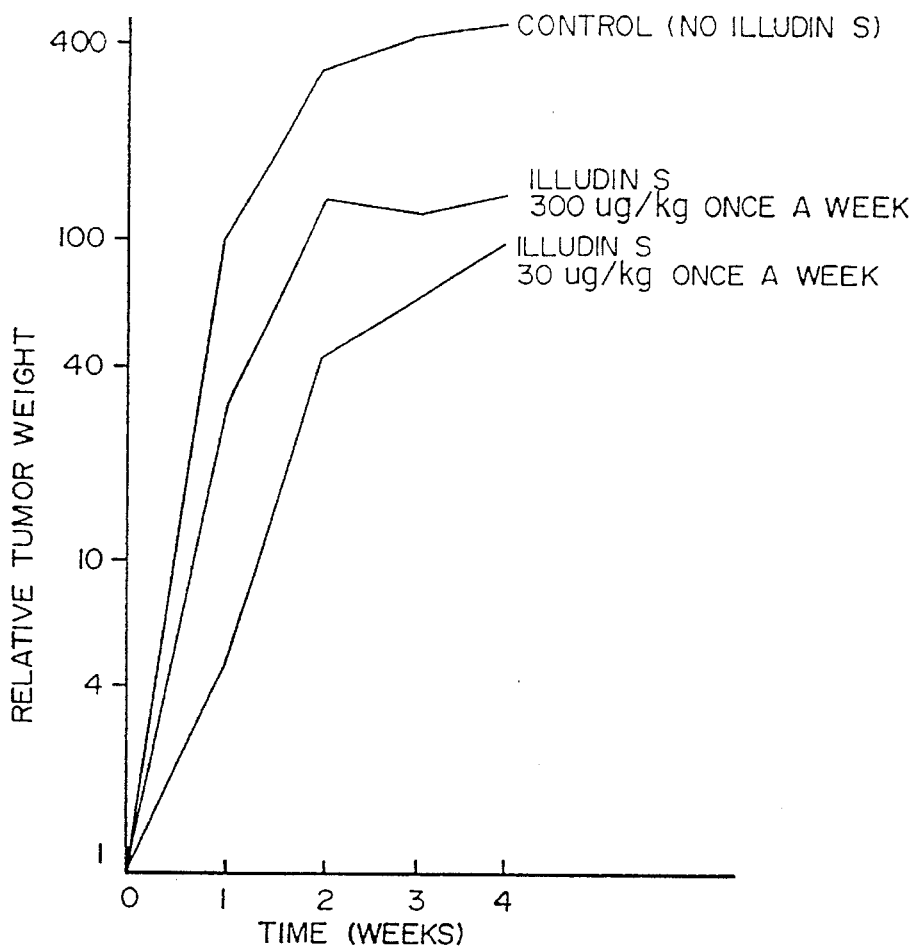
FIG. 4 shows the effect of illudin S on Molt-4 tumor growth in athymic mice (Balb/c).

Using procedures set forth in J. E. Leonard et al., Cancer Res., 47, 2899 (1987) and R. O. Dillman et al., Cancer Res., 45, 5632 (1985), both incorporated by reference herein, Molt-4 (human T-cell leukemia) xenografts were established in four week old athymic Balb/c nu/nu mice. After 3 weekly doses of total body radiation (600 cGy), mice were given subcutaneous flank injections of Molt4 cells together with irradiated (6000 cGy) HT-1080 feeder cells. Two animals received only irradiated HT-1080 feeder cells to ensure these cells did not induce tumors. Animals were monitored for Molt-4 tumor development and when tumors were palpable (approximately 4×4 mm at 5 to 7 days), mice were randomized into groups of 5 as previously described. Control mice received intraperitoneal saline and treated mice received either 300 µg/kg dehydroilludin M, IP twice weekly. In mice given illudin S there was tumor growth delay (FIG. 4).

Figure 5:
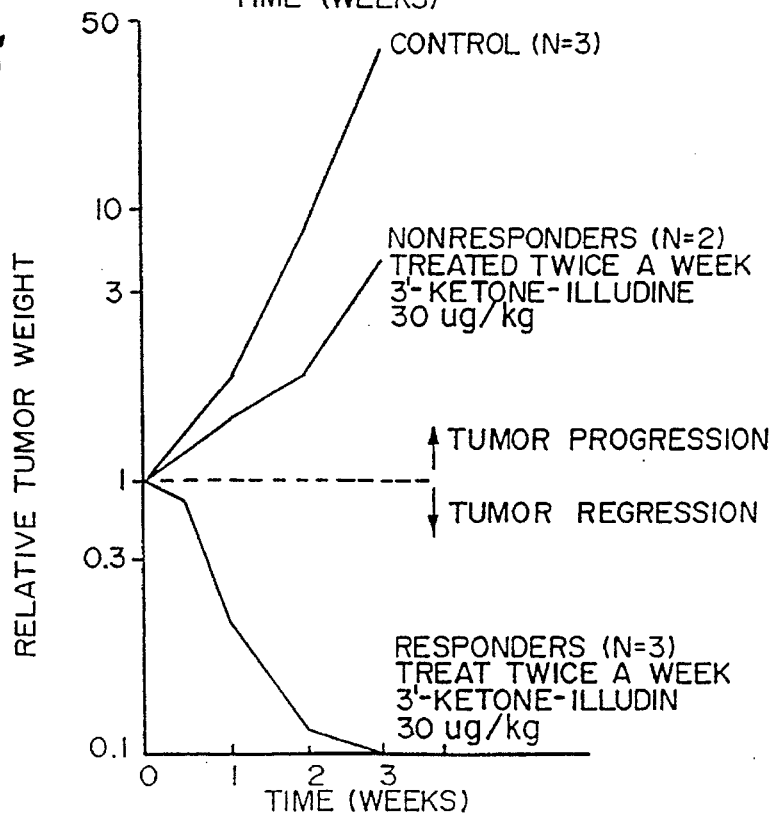
FIG. 5 shows the effect of dehydroilludin M on tumor growth.

In contrast, in nude mice which received the dehydroilludin M at the low dosage of 30 µg/kg (the compound was subsequently found to be nontoxic to mice at 60,000 µg/kg IP twice a week), three of five tumors underwent complete regression, but two tumors failed to respond (FIG. 5). The two apparently resistant tumors were harvested and tested in vitro for resistance to illudin S and dehydroilludin M. There was no evidence of resistance to either compound. Two of the complete responders were followed for over twelve weeks without evidence of tumor regression.

Using a different source of athymic nude mice, these experiments were repeated. In these studies there was little effect of illudins on tumor growth. The reason for this variability in response to Molt-4 xenografts probably relates to the low doses of dehydroilludin M, interanimal variations in glutathione metabolism, or drug distribution.

The efficacy of dehydroilludin M was then screened in a syngeneic model using murine SL-2 cells. SL-2 leukemia/lymphoma cells are injected subcutaneously and metastasized to lymph nodes, spleen, and lungs, and drug efficacy in this model is determined by increased life span (ILS). The SL-2 cells were administered at 2.5 million cells per animal and treatment was delayed. for 7 days until the tumors were palpable. Ibis is a relatively stringent test .against established tumors and contrasts to general drug screens in the SL-2 model which normally use only 0.5 million cells and starting drug treatment at 3 days. Dehydroilludin M had a little effect at 30 mg/kg IP twice a week, ILS 5%, and 60 mg/kg IP twice a week, ILS 18%. When administered IV at 0.03 mg/kg, twice a week, the ILS increased to 38%. This suggests the drug is metabolized by the liver and is likely more efficacious when administered IV.

During the course of these in vivo experiments, it became clear from in vitro experiments, that histiospecificity of illudins depends upon the presence of an active energy-dependent pump. The SL-2 and the Molt-4 cells were studied and it was determined that the uptake mechanism was not present. Therefore, the studies were redirected into xenograft models that used cells of myeloid lineage.

Figure 6:
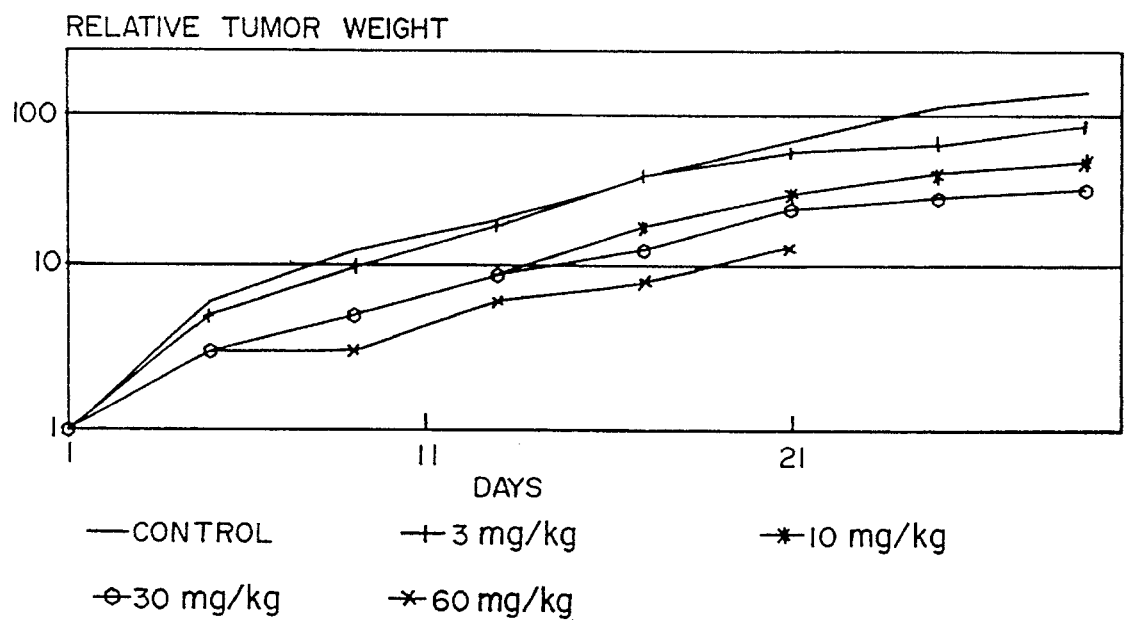
FIG. 6 shows the response of HL60/MRI xenograft to dehydroilludin M.
Figure 7:
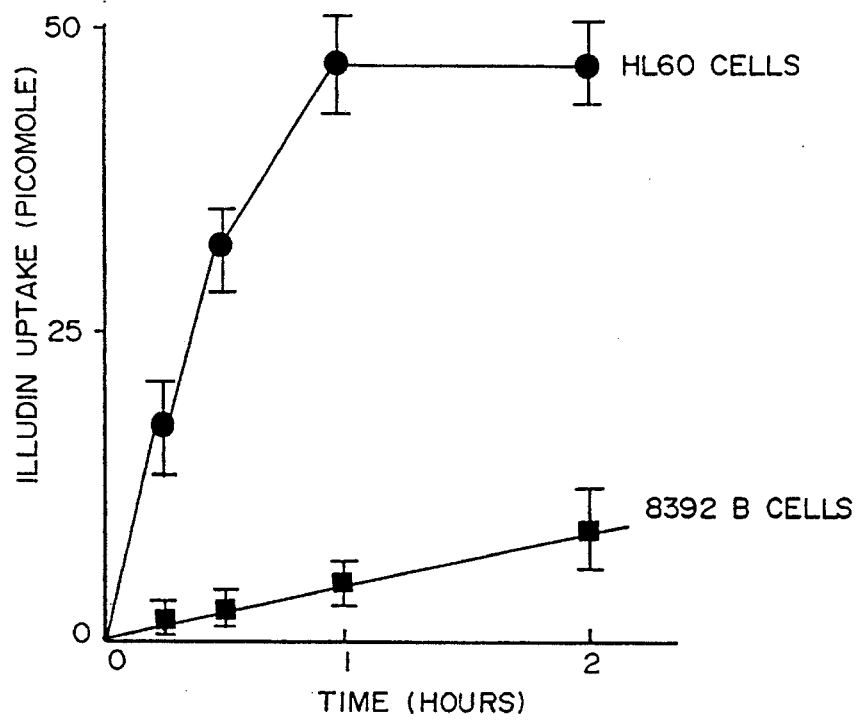
FIG. 7 shows illudin S uptake using relatively sensitive HL60 cells and resistant B cells.

Human HL-60 cells capable of growing as xenografts in nude mice without animal radiation were obtained from Dr. Theodore Brightman (NCI). These cells termed HL-60 MRI cells, were confirmed to have energy-dependent uptake pump, a not unexpected finding as their parental cells possess the pump. Dehydroilludin M induced dose related tumor inhibition when administered IP on a twice a week schedule (FIG. 6). The MTD IP dose for dehydroilludin M was reached in these studies on the 2 dosages per week IP dose schedule. Similar tumor regressions have been observed with IV dehydroilludin M.

In collaboration, the in vivo effects of dehydroilludin M was again studied. Initially the compound was studied against L1210 cells. A dose of 2.5 mg/kg IP given daily for 5 days resulted in an ILS of only 9%. The dehydroilludin M was then administered as a 24 hour infusion (5.0 mg/kg); the ILS was 11%. After we became aware of the presence of the energy-dependent uptake in human myelocytic cells, dehydroilludin M was screened for in vivo efficacy against a syngeneic mouse AML model using C1498 cells and a single bolus of illudin S, 2.5 mg/kg IP, produced an ILS of 35%. A second trial using the same dosage, administered IP once a day for 5 days resulted in a 44% ILS. As the animals can tolerate 60 mg/kg IP or 1 mg/kg IV (tail vein) on a twice a week schedule for 4 weeks without demonstrating weight loss or a decrease in food/water intake, it is possible to further optimize both dosage and treatment schedule.

EXAMPLE VII

HL60/MRI Mouse Experiment With Illudofulvene and Dehydroilludin M.

Thirty mice were injected subcutaneously, over the shoulder, with 500,000 HL60/MRI cells (human myeloid leukemia tumor cells). Treatment was begun on day 11, rather than immediately. This delay in starting treatment is a stringent test to determine whether a compound is effective. By delaying treatment, the tumor cells become firmly established.

The mice were divided into 6 groups of 5 each. One group was the control and these animals received on a placebo, the solution used to dilute the agent. The other groups received the following compounds and dosages: the dehydroilludin M compound at 10 mg/kg, the dehydroilludin M at 3.0 mg/kg, illudofulvene at 0.3 mg/kg, 1.0 mg/kg, and 3.0 mg/kg. All animals received the placebo or drugs by intravenous injection using a tail vein. The placebo or drugs were administered on a twice a week schedule.

Results are summarized in the accompanying Table 6. Both the dehydroilludin M and the illudofulvene compound were effective at inhibiting tumor growth and demonstrated dosage dependence inhibition (the more drug administered, the less the tumors grew). The animals receiving the highest amount of either drug did not display any evidence of adverse effect, such as a decrease in food or water intake, nor a statistically significant decrease in body weight. These results show that higher dosages of either drug can be administered. Also, that the drug could be administered on a more effective dosage schedule, such as on a daily basis.

TABLE 6

Summary: HL60/MRI experiment, intravenous - #1

| | BY TOTAL TUMOR WEIGHT [Mg] | | | | |
| --- | --- | --- | --- | --- | --- |
| | DAY 11 | DAY 18 | DAY 25 | DAY 32 | DAY 40 |
| CONTROL | | | | | |
| No Drug | $99 \pm 36$ | $845 \pm 282$ | $3299 \pm 1080$ | $10162 \pm 4123$ | $16747 \pm 5061$ |
| Dehydroilludin M | | | | | |
| 1 mg/kg IV | $114 \pm 55$ | $883 \pm 311$ | $2274 \pm 992$ | $6025 \pm 1772$ | $11507 \pm 3707$ |
| 3 mg/kg IV | $101 \pm 40$ | $911 \pm 309$ | $2127 \pm 1092$ | $2854 \pm 1260$ | $4784 \pm 2303$ |
| Illudofulvene | | | | | |
| 0.3 mg/kg IV | $73 \pm 38$ | $540 \pm 167$ | $1352 \pm 520$ | $3204 \pm 1147$ | $9501 \pm 4605$ |
| 1 mg/kg | $58 \pm 32$ | $582 \pm 297$ | $964 \pm 685$ | $2321 \pm 1434$ | $6275 \pm 2865$ |
| 3 mg/kg | $38 \pm 30$ | $369 \pm 250$ | $336 \pm 215$ | $437 \pm 238$ | $1201 \pm 501$ |

EXAMPLE VIII

Synthesis and Structure of 2,5,6,7-Tetramethyl-1-Indenone and Dehydropterosin Compounds.

First, 2,4,5,6-tetramethyl-1,3-indandione was synthesized by preparing a solution of 1,2,3-trimethylbenzene and methylmalonylchloride in carbon disulfide and adding aluminum trichloride portionwise over two hours. The mixture was refuxed for 2 more hours, crushed ice added, and extracted three times with chloroform. The combined extract was washed with brine, dried, and solvent removed to leave a residue which was purified by chromatography with 1% ethyl acetate in benzene. Removal of solvent and purification by sublimation gave the desired product.

The 2,5,6,7-tetramethyl-l-indenone was prepared by reducing 2,4,5,6-tetramethyl-1,3-indandione with zinc dust at 50° C. Product was purified by chromatography with 1% ethyl acetate in benzene to yield two isomers. The major isomer was treated with 10% potassium hydroxide, then purified by sublimation. The compound has the structure:

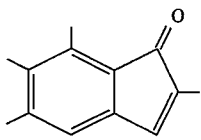

Dehydropterosin O synthesis: 3-acetoxy-6-(beta-methoxy) ethyl-2,5,7-trimethyl-1-indanone was dissolved in tetrahydrofuran and 10% potassium hydroxide and refluxed for two hours. The solution was then extracted three times with ether and the combined extracts chromatographed with 2% ethylacetate in benzene to yield the Dehydropterosin O compound. The compound has the structure:

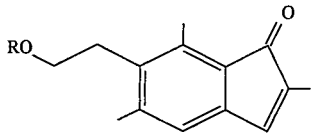

Both compounds were toxic to cells in vitro and have antifungal properties.

EXAMPLE IX

Synthesis of 6-hydroxymethylacylfulvene.

Illudofulvene (550 mg, 2.5 mmol) was dissolved in 40 mL THF and 30% formaldehyde-water solution (40 mL) was added. A 4 N $H_2SO_4$ solution (26.4 ml) was added to bring the final concentration of $H_2SO_4$ to 1 N. The solution was stirred overnight and extracted with ethyl acetate. The organic phase was washed with saturated $NaHCO_3$ solution, water and brine and dried over $MgSO_4$. Chromatography on silica gel with hexane and ethyl acetate gave 400 mg hydroxymethylfulvene (64%), which was crystallized from ethyl acetate hexane, m.p. 124°–126° C.; $^1$H NMR δ0.72 to 1.48 (m, 4 H), 1.38 (s, 3 H), 2.15 (s, 3 H), 2.19 (s, 3 H), 3.90 (s, 1 H), 4.66 (d, J=2.1 Hz, 2 H), 7.10 (s, 1 H. MS m/Z 246 (M+), 228 (M+-$H_2O$), 218 (M+-$CH_2CH_2$), 186 (M+-$CH_3$-$CH_2$-$CH_2$-OH), 185 (M+-$H_2O$-$CH_2CH_2$-$CH_3$). UV 233 nm (1.0×10$^4$), 325 nm (7.7×10$^3$). The compound has the structure:

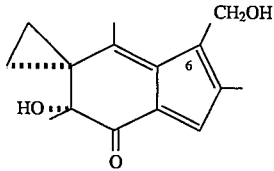

EXAMPLE X

Synthesis of 6-Iodoacylfulvene.

To a solution of illudofulvene (60 35 mg, 0.28 mmol) in 15 ml $CH_2Cl_2$ was added silver trifluoroacetate (63 mg, 0.29 mmol). A solution of iodine (70.5 mg, 0.28 mmol) in a 8 mL $CH_2Cl_2$ was added dropwise at 0° C. The mixture was stirred at that temperature for 3 hours then filtered through celite and eluted with ether. Concentration of the filtrate gave iodoacylfulvene as a red gum (73 mg, 77%). $^1$H NMR a 0.76 to 1.54 (m, 4 H), 1.38 (s, 3 H), 2.14 (s, 3 H), 2.36 (s, 3 H), 3.87 (s, 1 H), 7.16 (s, 1 H). MS m/Z 342 (M+), 314 (M+-$CH_2CH_2$), 299 (M+-$CH_{CH2}$-$CH_3$), 29 6 (M+-$CH_2CH_2$-$H_2O$), 215 (M+-I), 187 (M+-I-$CH_2CH_2$), 127 (I+). The compound has the structure:

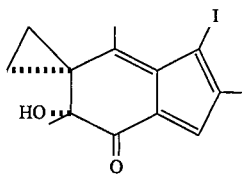

EXAMPLE XI

6-Bromoacylfulvene.

Illudofulvene (60 mg, 0.28 mmol) was dissolved in 9 ml acetonitrile at 0° C. N-bromosuccinimide (50 mg, 0.28 mmol) was added and the mixture was stirred at that temperature for 3.5 hours. Water was used to quench the reaction and ether to extract the product. The ether layer was washed with water and brine and dried over $MgSO_4$. Chromatography gave bromoacylfulvene as orange crystals (77 mg, 94%; recrystallized from ether acetate-hexane, m.p.. (92°–94° C.). $^1$H NMR δ0.75 to 1.55 (m, 4 H), 1.40 (s, 3 H), 2.12 (s, 3 H), 2.33 (s, 3H), 3.89 (s, 1 H), 7.15 (s, 1 H). MS m/Z 295 (M+), 267, 265, (M+-$CH_2CH_2$), 252, 250 (M+-$CH_2CH_2$-$CH_3$), 249, 247 (M+-$CH_2CH_2$-$H_2O$), 215 (fulvene-1). The compound has the structure:

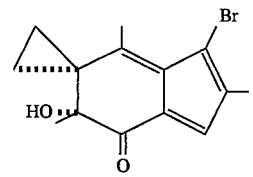

EXAMPLE XII (6-(p-Hydroxybenzyl)acylfulvene.

Phenol (40 mg, 0.4 mmol) was added to a solution of 6-hydroxymethylacylfulvene (70 rag, 0.28 mmol) in dry $CH_2Cl_2$ (25 mL). The mixture was cooled to −78° C. and boron trifluoride etherate (0.3 mL, 2.7 mmol) was added dropwise. The reaction was stirred at that temperature for 1 hour and water was added to quench the reaction. The organic layer was washed with $H_2O$, $NaHCO_3$ and brine, and dried over $MgSO_4$. Chromatography on silica gel with hexane-ethyl acetate yielded 90 mg (98%) of red crystals (m.p. 143°–144° C.). $^1$H NMR δ0.59–1.43 (m, 4 H), 1.36 (s, 3 H), 1.76 (s, 3 H), 2.07 (s, 3 H), 3.95 (s, 1 H), 3.97 (d, J=7.2 Hz, 2 H), 4.83 (s, 1 H), 6.74 (d, J=8.4 Hz, 2 H), 6.91 (d, J=8.4 Hz, 2 H), 7.22 (s, 1 H). MS m/Z 322 (M+), 294 (M+-2 $CH_2$), 279 (M+-2 $CH_2$-$CH_3$), 251 (M+-2 $CH_2$-$CH_3$-CO), 215, 107. UV 228 nm 1.2×10$^4$, with inflections at 243 and 262 nm), 325 (7.1×10$^3$), 410 nm (2.6×10$^3$). The compound has the structure:

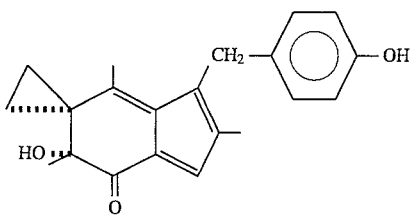
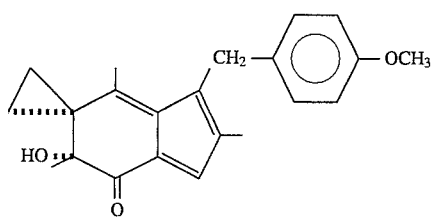

EXAMPLE XIII

6-(p-Methoxybenzylcylfulvene.

Anisole (0.04 mL, 0.37 mmol) was added to a solution of 6-hydroxymethylacylfulvene (10 mg, 0.04 mmol) in dry $CH_2Cl_2$ (5 mL). The mixture was cooled to −78° C., and boron trifluoride etherate (0.04 mL, 0.36 mmol) was added dropwise. The reaction was stirred at that temperature for 1 hour and water was added to quench the reaction. The organic layer was washed with $H_2O$, saturated $NaHCO_3$ and brine, and dried over $MgSO_4$. Concentration of the solution gave a residue which was dried in vacuo, yielding the product in quantitative yield (14 mg). $^1H$ NMR δ0.59–1.40 (m, 4 H). 1.36 (s, 3 H), 1.76 (s, 3 H), 2.07 (s, 3 H), 3.78 (s, 3 H), 3.95 (s, 1 H), 3.99 (d, J=16.12 Hz, 2 H), 6.81 (d, J=8.8 Hz, 2 H), 6.96 (d, J=8.3 Hz, 2 H), 7.22 (s, 1 H). MS m/Z 336 (M+), 308 (M+−$CH_2CH_2$), 215, 121. UV 410 nm {2.7×10$^3$}, 325 nm (7.0×10$^3$), 267 nm (1.0×10$^4$), 245 nm (inflection), 226 nm (1.9×10$^4$), 203 nm (1.4×10$^4$). The compound has the structure:

EXAMPLE XIV

In Vitro Cell Culture Studies of Acylfulvene Analogs.

In vitro testing using cell culture assays demonstrated the 6-hydroxymethylacylfulvene, bromoacylfulvene, and iodoacylfulvene analogs were markedly toxic to the target tumor cells HL60 and MV522 at both 2 and 48 hour exposure periods (Table 8 and Table 9). The relative toxicity ratio (2 to 48 hour toxicity) suggested these analogs would be more efficacious in vivo than either the parent Illudin S compound.

TABLE 8

| 2 hour cytotoxicity of new analogs (as determined by inhibition of thymidine incorporation compared to original analogs and Illudin S | | | |
|---|---|---|---|
| | Two hour IC50 values (nanomoles/liter) | | |
| | HL60 Cells | 8392 Cells | MV522 |
| Illudin S | 10 ± 1 | 236 ± 2 | 19 ± 6 |
| Dehydroilludin M | 377 ± 81 | 61,335 ± 13,006 | 1,826 ± 378 |
| Illudofulvene | 998 ± 244 | 66.435 ± 13,006 | 727 ± 180 |
| 6-hydroxymethylacylfulvene (6-HMAF) | 150 ± 11 | 7,359 ± 2,096 | 114 ± 28 |
| 6-acetoxymethylacylfulvene | 3,333 ± 192 | 47,455 ± 2,951 | 1,066 ± 87 |
| bromoacylfulvene | 803 ± 88 | 17.175 ± 890 | 4,180 ± 424 |
| iodoacylfulvene | 2,602 ± 345 | 10,331 ± 497 | 956 ± 152 |
| 6-(p-hydroxybenzyl)acylfulvene | 264 ± 38 | 95,236 ± 11,984 | 1,180 ± 180 |
| 6-(p-methoxybenzyl)acylfulvene | 1,964 ± 84 | 35,714 ± 7,292 | 2,045 ± 208 |

| 48 hour cytotoxicity of new analogs compared to original analogs and the parent Illudin S compound | | | |
|---|---|---|---|
| | 48 hour IC50 values (nanomoles/liter) | | |
| | HL60 Cells | 8392 Cells | MV522 |
| Illudin S | 10 ± 1 | 8 ± 2 | 4 ± 1 |
| Dehydroilludin M | 296 ± 66 | 269 ± 100 | 313 ± 23 |
| Illudofulvene | 364 ± 74 | 833 ± 152 | 349 ± 23 |
| 6-hydroxymethylacylfulvene | 4 ± 1 | 76 ± 4 | 73 ± 8 |
| 6-acetoxymethylacylfulvene | 806 ± 30 | 4,434 ± 163 | 486 ± 42 |
| 6-bromoacylfulvene | 412 ± 21 | 1,186 ± 138 | 356 ± 61 |
| 6-iodoacylfulvene | 290 ± 12 | 1,696 ± 183 | 556 ± 47 |
| 6-(p-hydroxybenzyl)acylfulvene | 382 ± 39 | 11,078 ± 388 | 615 ± 56 |
| 6-(p-methoxybenzyl)acylfulvene | 1,051 ± 104 | 7,143 ± 244 | 1,548 ± 214 |

EXAMPLE V

In Vivo Studies.

Figure 8:
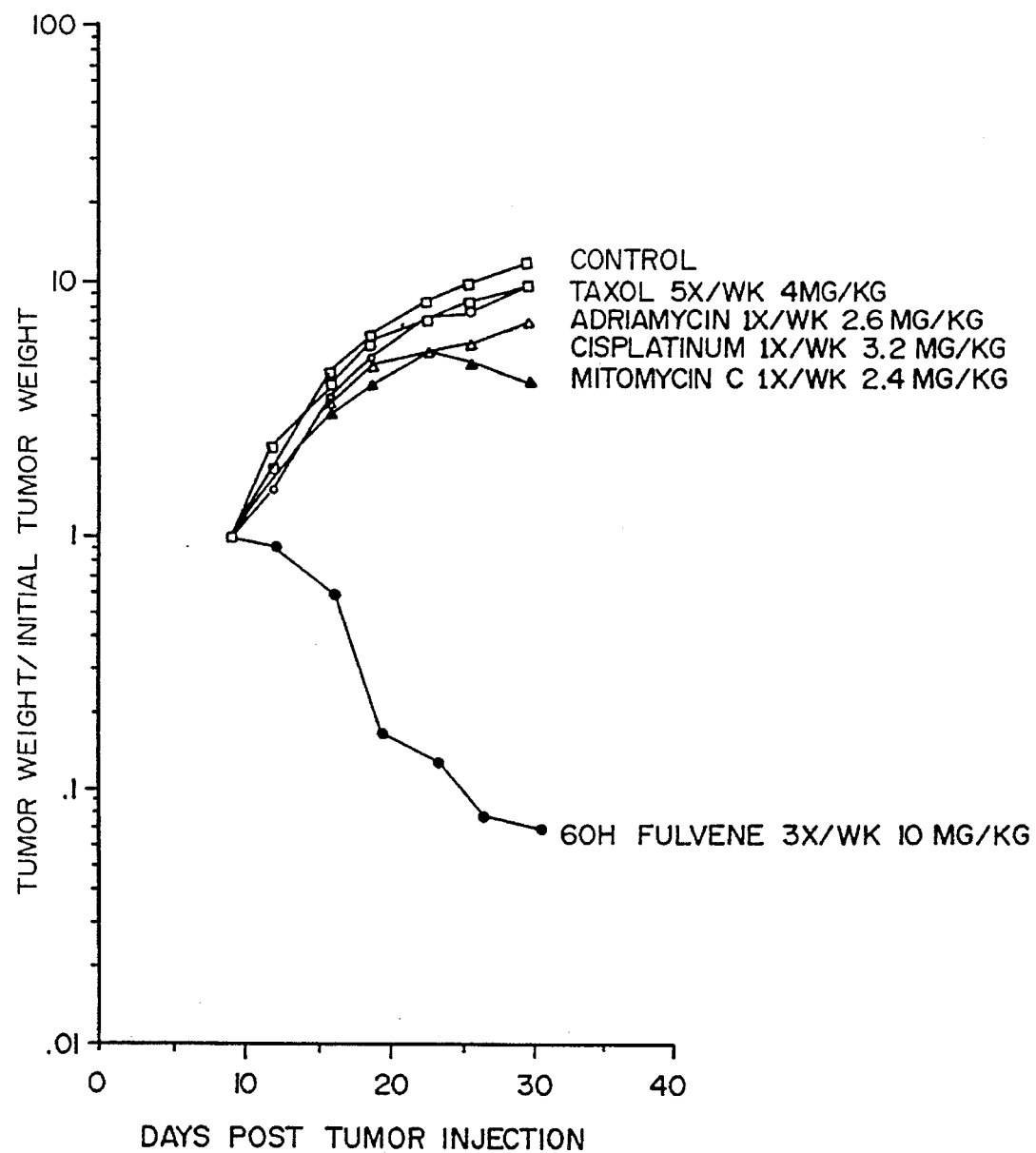
FIG. 8 shows the effect of 6-hydroxymethylacylfulvene and other conventional anticancer agents on human adenocarcinoma MV522.

Based on these in vitro screening results, one of the analogs, the 6-hydroxymethylacylfulvene, was chosen for in vivo studies to determine if the analog was indeed more potent than the acylfulvene. The xenograft was again the human lung adenocarcinoma MV522 as it is a nonresponsive model to conventional anti-cancer agents and kills by metastasis (not local tumor invasion). The conventional anti-cancer agents cis-platinum, taxol, mitymycin C, adriamycin, as well as Illudin S were chosen as pharmaceutical controls. A control group was included that received only the solvent used to dissolve the drugs, a 40% dimethylsulfoxide/ normal saline mixture (40% DMSO/NS). The 6-hydroxymethylacylfulvene analog actually induced tumor regression in animals. Actual regression of tumors by an anticancer agent has never been noted before in this model. There was no inhibition of tumor growth by conventional anticancer agents or by Illudin S (FIG. 8). Animals received only 9 doses of the 6-hydroxymethylacylfulvene analog. There was no evidence of toxic side effects in these animals as evidenced by a decrease in activity, weight gain, food intake, or water intake. There was no significant increase in the life span of cisplatinum, taxol, mitomycin C, and Adriamycin treated animals as compared control (DMSO/NS) treated animals. The illudin S actually caused premature death (drug toxicity) (Table 10). The 6-hydroxymethylacylfulvene treated animals lived significantly longer than controls (DMSO/NS treated), cisplatinum, taxol, mitomycin C, and Adriamycin treated animals (p<0.001 for all groups) (Table 10).

TABLE 10

Efficacy of 6-hydrocymethylacylfulvene analog, versus other agents, in the human lung adenocarcinoma MV522 metastatic lung tumor model - First experiment

| drug | | life span |
| --- | --- | --- |
| controls DMSO/NS IP 3X/WK | | 100 ± 7% |
| cis-platinum | 3.2 mg/kg IP 1X/WK | 102 ± 8% |
| taxol | 4.0 mg/kg IP 5X/WK | 100 ± 10% |
| mitomycin C | 2.4 mg/kg IP 1X/WK | 111 ± 2% |
| Adriamycin | 2.6 mg/kg IP 1X/WK | 98 ± 12% |
| Illudin S | 2.5 mg/kg IP 3X/WK | <26% |
| | | [5/5 dead at only 3 doses] |
| 6-hydroxymethylacylfulvene | 10 mg/ kg IP 3X/WK | 233 ± 18% |

Figure 9:
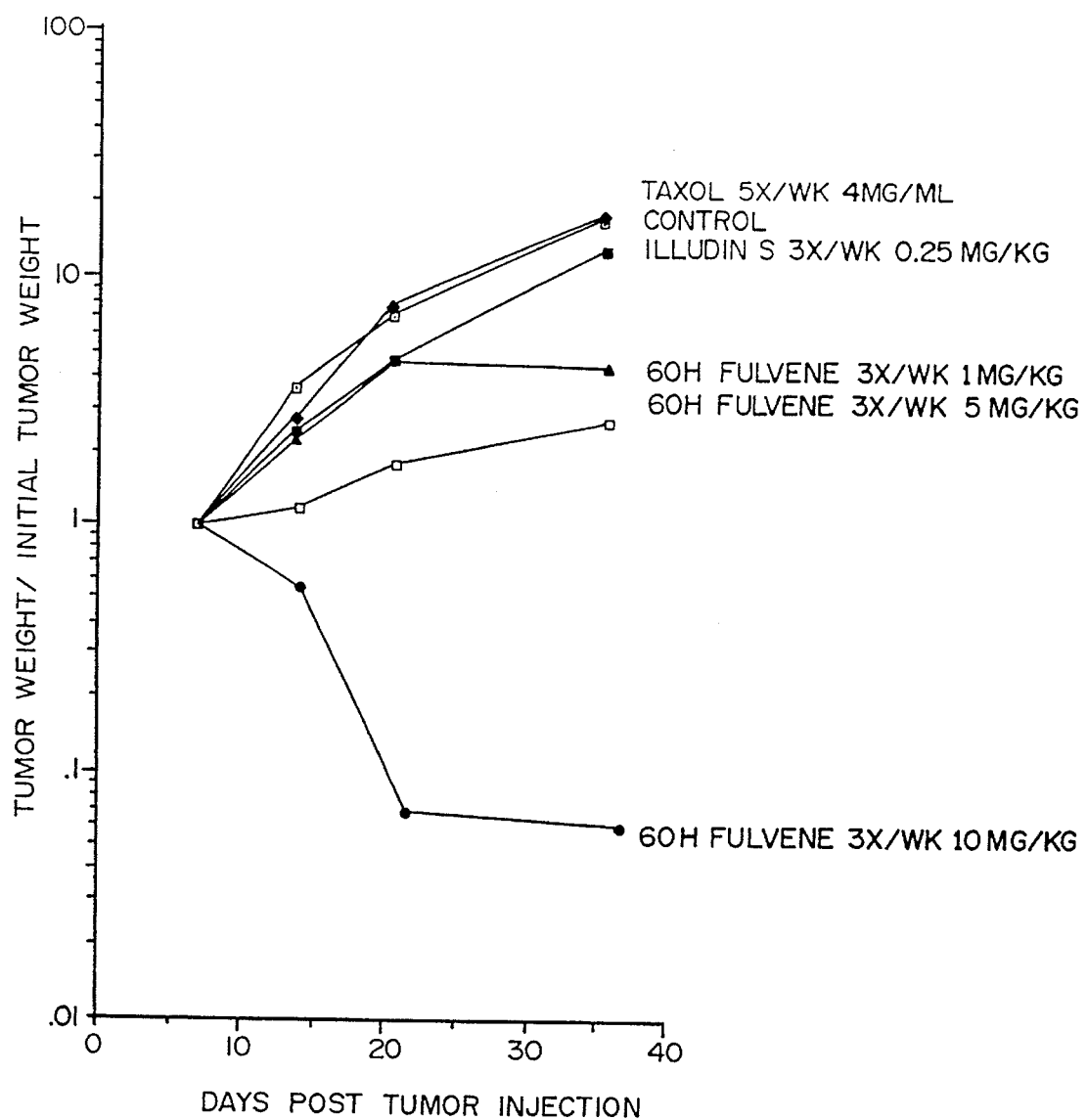
FIG. 9 shows the effect of different doses of 6-HMAF on human (lung adenocarcinoma MV522.

The experiment was repeated with different dosages of the 6-hydroxymethylacylfulvene analog to determine if a dose-response pattern was present. Taxol and low dose illudin S were again included as pharmaceutical controls (Table 11). A control group receiving only the pharmaceutical solvent (40% DMSO/NS) was again included. Tumor regression was again noted at 10 mg/kg, and inhibition of tumor growth was noted with 1 and 5 mg/kg treatment. The taxol and low dose Illudin S again failed to inhibit tumor growth (FIG. 9). In this second experiment there was again no significant increase in the life span of taxol or Illudin S treated animals as compared controls (40% DMSO/NS treated animals). The 10 mg/kg 6-hydroxymethylacylfulvene and 5 mg/kg 6-hydroxymethylacylfulvene treated animals lived significantly longer than controls (DMSO/NS treated), taxol, or Illudin S treated animals. The probability (or significance) value for 10 mg/kg 6-hydroxymethylacylfulvene-treated animals versus the controls, taxol treated, and Illudin S treated animals was less than 0.001 in each case (p< 0.001). The probability value for the 5 mg/kg 6-hydroxymethylacylfulvene treated animals versus the controls, taxol treated, and Illudin S treated animals was also less than 0.001 in each case (p<0.001). The 1 mg/kg 6-hydroxymethylacylfulvene treated animals also lived significantly longer than the control group (p<0.01).

TABLE 11

Efficacy of 6-hydroxymethylacylfulvene anaolg, versus other agents, in the human lung adenocarcinoma MV522 metastatic lung tumor model - Second experiment

| | drug | life span |
| --- | --- | --- |
| controls DMSO/NS IP 3 X/WK | | 100 ± 16% |
| | | (100% by definition) |
| taxol | 4.0 mg/kg IP 5X/WK | 120 ± 10% |
| | | (not significant) |
| Illudin S | 0.25 mg/kg IP 3X/WK | 104 ± 20% |
| 6-hydroxymethylzcylfulvene | 10 mg/kg IP 3X/WK | 232 ± 20% |
| 6-hydroxymethylacylfulvene | 5 mg/kg IP 3X/WK | 154 ± 13% |
| 6-hydroxymethylacylfulvene | 1 mg/kg IP 3X/WK | 135 ± 10% |

The experiment was repeated for a third time (Table 12). The amount of taxol administered IP was increased to demonstrate maximum dosage, and a subcutaneous dosage was added due to reports that this route may be more efficacious. Adriamycin and mitomycin C were again included. Two of the new acylfulvene derivatives (iodoacylfulvene and the (p-hydroxybenzyacylfulvene) were included in this experiment. The diketone analog was included to demonstrate the marked improvement of the 6-hydroxymethylacylfulvene. The 6-hydroxymethylacylfulvene markedly increased the life span versus controls and all other drug treated animals. The probability (or significance) value for the 6-hydroxymethylacylfulvene versus all the control group, the mitomycin C treated group, the adriamycin treated group, and both of the taxol treated groups was less than 0.0005 (p< 0.0005). This is an extremely significant effect. It is important to note that based on the longevity of 2 particular animals, there is the possibility they may have been cured. Although the diketone also markedly increased the lifespan versus controls (p< 0.002) and other drug treated animals, it was not as effective as the 6-hydroxymethylacylfulvene. Note that the lifespan of the high dose taxol treated animals (6 mg/kg IP) not only decreased below that of the 4 mg/kg taxol treated animals in the previous experiment, but it was now less than the life span of untreated or control animals. This indicates that the maximum dose for taxol had been reached and drug toxicity was now killing the animals. The other new analogs, the bromoacylfulvene and the p-hydroxybenzylacylfulvene are also effective in this model.

TABLE 12

Efficacy of 6-hdyroxymethylacylfulvene anaolg, versus other agents, in the human lung adenocarcinoma MV 522 metastatic lung tumor model - Third experiment

| Compound | Dose | life span |
| --- | --- | --- |
| controls DMSO/NS IP 3X/WK | | 100 ± 29% |
| taxol | 6.0 mg/kg IP 5X/WK | 93 ± 22% |
| taxol | 20.0 mg/kg IP 5X/WK | 113 ± 22% |
| mitomycin C | 2.4 mg/kg IP 1X/WK | 149 ± 12% |
| adriamycin | 2.6 mg/kg IP 1X/WK | 150 ± 25% |
| diketone | 30 mg/kg IP 3X/WK | 163 ± 6% |
| (listed original application) | | |
| iodacylfulvene | 20 mg/kg IP 3X/WK | 120 ± 34% |
| p-hydroxybenzlacylfulvene | 15 mg/kg IP 3X/WK | 125 ± 16% |
| p-hydroxybenzyacylfulvene | 20 mg/kg IP 3X/WK | 126 ± 22% |
| 6-hydroxymethylacylfulvene | 10 mg/kg IP 3X/WK | >204% |
| | | (2 animals alive, ? cured)— |

EXAMPLE XVI

MX-1 Human Breast Tumor Xenograft.

Nude mice are implanted subcutaneously (s.c.) by trocar with fragments of MX-1 mammary carcinomas harvested from s.c. growing MX-1 tumors in nude mice hosts. When tumors are approximately 5 mm×5 mm in size (usually about ten days after inoculation), the animals are pair-matched into treatment and control groups. Each group contains 10 tumored mice, each of which is eartagged and followed individually throughout the experiment. The administration of drugs or vehicle begins the day the animals are pair-matched (day 1). The doses, route of drug administration and schedule are selected as appropriate for the study in question, If the maximum tolerated dose (MTD) of an agent is not known, it was determined in an initial dosing experiment in non-tumored mice. In a typical experiment, drugs are given at their MTD and ½ MTD doses i.p. on a daily×5 schedule.

The experiment is usually terminated when control tumors reach a size of 2–3 g. Mice are weighed twice weekly, and tumor measurements are taken by calipers twice weekly, starting on day 1. These tumor measurements are converted to mg tumor weight by a well-known formula, and from these calculated tumor weights the termination date can be determined. Upon termination, all mice are weighed, sacrificed, and their tumors excised. Tumors, are weighed, and the mean tumor weight per group is calculated. In this model, the mean treated tumor weight/mean control tumor weight×100% (T/C) is subtracted from 100% to give the tumor growth inhibition (TGI) for each group).

Some drugs cause minor shrinkage in the MX-1 model. With these agents, the final weight of a given tumor is subtracted from its own weight at the start of treatment on day 1. This difference divided by the initial tumor weight is the % shrinkage. A mean % tumor shrinkage can be calculated from data from the mice in a group that experienced MX-1 regressions. If the tumor completely disappears in a mouse, this is considered a complete regression or complete tumor shrinkage. If desired, mice with partial or total tumor regressions can be kept alive past the termination date to see whether they live to become long term, tumor-free survivors.

HMAF was evaluated against the MX-1 mammary carcinoma xenograft at the MTD of 7.5 mg/kg, and also at 5.0 mg/kg, i.p. daily×5, delivered in 10% cremophor, 20% ethanol and 70% isotonic saline. The 7.5 mg mg/kg dose caused no lethality, or unacceptable weight loss to the nude mice (day 8 weight loss= 9.5%). The compound was strikingly efficacious at its MTD, causing complete tumor regressions in 4 mice, and an average 91% tumor shrinkage in the other 6 mice in that group. The 5.0 mg/kg dose produced 2 complete regressions, and an average 88% tumor shrinkage in the other 8 mice.

While in vitro activity of novel compounds, such as HMAF, against models such as P388 and L1210 may identify drugs active against rapidly growing tumors, the MX-1 xenograft model was introduced as an in vivo screen since it exhibits greater potential to identify agents active against slowly growing, solid minors. Total tumor regressions of established MX-1 tumors are unusual, indicating that HMAF may have important activity against solid tumors resistant to conventional chemotherapeutic agents. Furthermore, this may be a general property of this compound since HMAF shows similar activity against the drug-resistant MV522 lung cancer xenograft (Tables 11 and 12).

EXAMPLE XVI

P388 Leukemia.

HMAF was also evaluated against P388 leukemia in mice. The tumor inoculum is prepared by removing ascites fluid containing P388 cells from tumored B6D2F1 mice, centrifuging the cells, and then resuspending the leukemia cells in saline. Mice receive $1 \times 10^6$ P388 cells i.p. on day 0. Initial dosing experiments on a daily×5 schedule in B6D2F1 mice established the MTD of HMAF as 7.5 mg/kg. HMAF was tested at doses of 7.5 and 5.0 mg/kg vs. the P388 leukemia model. Modest efficacy was observed with HMAF vs. P388; treated/control (T/C) values of 140 and 137 were obtained with doses of 6.5 and 5.9 mg/kg, respectively. A T/C value of 150 means that treated mice lived 50% longer than the controls. Weight loss at the higher dose was 13% on day 8, again confirming that 7.5 mg/kg is the MTD for this agent on the daily×5 schedule. HMAF was inactive against B16 melanoma in mice at the same doses.

EXAMPLE XVII

In Vitro Assays

HMAF exhibited relatively weak activity against B16 melanoma with IC50 values of 3.73–4.65 µg/ml. HMAF was about one log more potent against the murine P388 cells in vitro, with an IC50 value of 0.16–0.32 µg/ml. Interestingly, HMAF was very potent against the two human tumor cell lines tested (HT-29 human colon tumor and MCF-7 human breast tumor), with IC50 values ranging from 0.036–0.070 µg/ml. This data is summarized in Table 13 below.

TABLE 13

| Cell Line: | HMAF IC50 (µg/ml) | | | |
|---|---|---|---|---|
| | B16 | HT29 | P388 | MCF-7 |
| | 4.65 | 0.050 | 0.165 | 0.036 |
| | 3.73 | 0.076 | 0.319 | 0.043 |

All patent and publications cited herein are incorporated by reference. Although the invention has been described with reference to the presently-preferred embodiment, it should be understood that various modifications can be made without departing from the spirit of the invention. Accordingly, the invention is limited only by the following claims.

What is claimed is:

1. A compound of the formula (I):

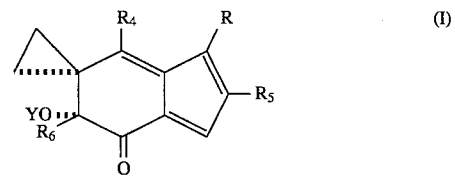

wherein $R_4$, $R_5$ and $R_6$ are $(C_1-C_4)$alkyl, Y is H $(C_1-C_3)$alkyl, $(R_4)(R_5)(R_6)$Si or $(C_1-C_4)$alkylC(O) and R is $CH_2OH$, halo, benzyl optionally substituted with OY, $CH_2OCH_2OH$, or $CH_2OC(O)R_7$, wherein $R_7$ is $(C_1-C_4)$alkyl, $(C_6-C_{12})$aryl or $N(X)_2$, wherein each X is H or $(C_1-C_2)$alkyl, and the pharmaceutically-acceptable salts thereof.

2. A compound of claim 1 wherein $R_4$, $R_5$ and $R_6$ are $CH_3$.

3. A compound of claim 1 wherein Y is H.

4. A compound of claim 1 wherein R is $CH_2OH$ or $CH_2OC(O)CH_3$.

5. A compound of claim 1 wherein R is benzyloxymethyl or 4-hydroxybenzyloxymethyl.

6. A compound of claim 1 wherein R is Br or I.

7. A pharmaceutical unit dosage form comprising an effective tumor growth inhibiting amount of the compound of claim 1 in combination with a pharmaceutically-acceptable carrier.

8. The pharmaceutical unit dosage form of claim 7 wherein the carrier is a liquid vehicle.

9. The pharmaceutical unit dosage form of claim 8 wherein the carrier is adapted for parenteral administration.

10. The pharmaceutical unit dosage form of claim 9 which is adapted for intravenous administration.

11. The pharmaceutical unit dosage form of claim 7 which is adapted for oral administration.

12. The pharmaceutical unit dosage form of claim 7, which is a tablet or a capsule.

* * * * *